United States Patent [19]

Bacus et al.

[11] Patent Number: 5,109,429

[45] Date of Patent: Apr. 28, 1992

[54] APPARATUS AND METHOD FOR ANALYSES OF BIOLOGICAL SPECIMENS

[75] Inventors: James W. Bacus, Hinsdale; Peter S. Oud, Naperville, both of Ill.

[73] Assignee: Cell Analysis Systems, Inc., Lombard, Ill.

[21] Appl. No.: 99,141

[22] Filed: Sep. 21, 1987

Related U.S. Application Data

[63] Continuation of Ser. No. PCT/US86/02411, Nov. 4, 1986, which is a continuation-in-part of Ser. No. 76,685, Jul. 2, 1987, abandoned, which is a continuation-in-part of Ser. No. 794,937, Nov. 4, 1985, Pat. No. 4,741,043.

[51] Int. Cl.⁵ .............................................. G06K 9/00
[52] U.S. Cl. .................................. 382/6; 364/413.08; 364/413.09
[58] Field of Search ............... 206/456; 382/6, 8, 1; 358/101; 356/39, 244, 256; 128/637, 633; 350/534, 535, 536, 529; 364/413.13, 413.08, 413.07, 413.09, 413.1; 436/15–17, 2, 43; 424/3, 5, 94.1; 427/2

[56] References Cited

U.S. PATENT DOCUMENTS

| | | | |
|---|---|---|---|
| 3,297,869 | 1/1967 | Meyer | 250/440.1 |
| 3,481,659 | 12/1969 | Rosenberg | 350/535 |
| 3,532,412 | 10/1970 | Miller | 350/536 |
| 3,773,425 | 11/1973 | Bentley | 356/126 |
| 3,847,486 | 11/1974 | McCabe | 356/205 |
| 3,907,437 | 9/1975 | Hirschfeld | 356/156 |
| 3,977,971 | 8/1976 | Weber et al. | 356/168 |
| 4,000,417 | 12/1976 | Adkisson et al. | 250/201 |
| 4,017,192 | 4/1977 | Rosenthal | 356/201 |
| 4,045,772 | 8/1977 | Bouton et al. | 340/146.3 |
| 4,048,616 | 9/1977 | Hart et al. | 340/146.3 |
| 4,097,845 | 6/1978 | Bacus | 340/146.3 |
| 4,125,828 | 11/1978 | Resnick et al. | 340/146.3 |
| 4,129,854 | 12/1978 | Suzicki et al. | 340/146.3 |
| 4,132,767 | 1/1979 | Tohmatsu et al. | 424/1.1 |
| 4,152,410 | 5/1979 | Ishii | 424/1.1 |
| 4,160,817 | 7/1979 | Bucovaz et al. | 424/1.1 |
| 4,174,178 | 11/1979 | Ouchi et al. | 356/39 |
| 4,175,860 | 11/1979 | Bacus | 382/6 |
| 4,199,743 | 4/1980 | Bacus | 340/146.3 |
| 4,207,554 | 6/1980 | Resnick et al. | 340/146.3 |
| 4,213,036 | 7/1980 | Kopp et al. | 235/92 |
| 4,219,440 | 8/1980 | Runck et al. | 252/408 |
| 4,227,814 | 10/1980 | Soodak et al. | 356/410 |
| 4,231,660 | 11/1980 | Remey et al. | 356/244 |
| 4,232,001 | 11/1980 | Jensen et al. | 424/1.1 |
| 4,232,970 | 11/1980 | Sawamura et al. | 356/39 |
| 4,257,709 | 3/1981 | Mostyn | 356/435 |
| 4,307,376 | 12/1981 | Miller et al. | 340/146.3 |
| 4,362,386 | 12/1982 | Matsushita et al. | 356/39 |
| 4,389,669 | 6/1983 | Epstein et al. | 358/101 |
| 4,404,683 | 9/1983 | Kobayashi | 382/6 |
| 4,408,231 | 10/1983 | Bushaw et al. | 358/280 |
| 4,435,027 | 3/1984 | Dolbeare | 312/222 |
| 4,446,871 | 5/1984 | Imura | 128/633 |
| 4,453,266 | 6/1984 | Bacus | 382/6 |
| 4,513,438 | 4/1985 | Graham et al. | 382/6 |
| 4,523,278 | 6/1985 | Reinhardt et al. | 364/413 |
| 4,562,593 | 12/1985 | Ooe et al. | 382/6 |
| 4,592,089 | 5/1986 | Hartmann et al. | 382/6 |
| 4,741,043 | 4/1988 | Bacus | 382/6 |
| 4,812,412 | 3/1989 | Turner | 436/15 |

FOREIGN PATENT DOCUMENTS 59-88716  5/1984  Japan .

OTHER PUBLICATIONS

King and Greene, *Monoclonal antibodies localize oestrogen receptor in the nuclei of target cells,* Nature 307:745–747, 1984.

Jensen, et al., *Receptors Reconsidered: A 20-Year Perspective,* Recent Progress in Hormone Research 38:1–39.

(List continued on next page.)

*Primary Examiner*—Michael Razavi
*Attorney, Agent, or Firm*—Fitch, Even, Tabin & Flannery

[57] ABSTRACT

A kit for the quantitation of components in cell nuclei is described wherein the kit includes a stain and microscopic slides. Each slide has reference cell objects and a specimen cell area for receipt of specimen cells which are stained simultaneously with the reference cell objects.

37 Claims, 2 Drawing Sheets

OTHER PUBLICATIONS

*UN Convention on Contracts for the International Sale of Goods to Enter Into Force,* ASIL News, p. 3, Jan./Feb. 1987.

*Monoclonal antibodies to human estrogen receptor,* Proc. Natl. Acad. Sci. U.S.A. 77:5115–5119, 1980.

Gorell, et al., *Purification of nuclear estrogen receptors,* Int. Congr. Ser. Excerpta Med. 1977.

James and Goldstein, *Haemoglobin Content of Individual Erythrocytes in Normal and Abnormal Blood,* Jrl. of Haemotology 28:89–102, 1974.

McCarty, et al., *Estrogen Receptor Analysis,* Arch Pathol Lab Med 109:716–721, 1985.

*Immunocytochemical Assay for the Detection of Human Estrogen Receptor,* Abbott Laboratories, 83-1547/R2, 1986.

Sherrod and Taylor, *Nonlymphocyte Tumor Markers in Tissues,* Immunopathology and Immunohistology, Chapter 145, pp. 938–947.

King, et al. *Comparison of Immunocytochemical and Steroid-binding Assays for Estrogen Receptor in Human Breast Tumors,* Cancer Research 45:293–304, 1985.

WO-A 702 803 (Cell Analysis Systems, Inc.)–International Patent Publication.

WO-A-8 301 779 Reanal Finomvegyszergyar–International Patent Publication.

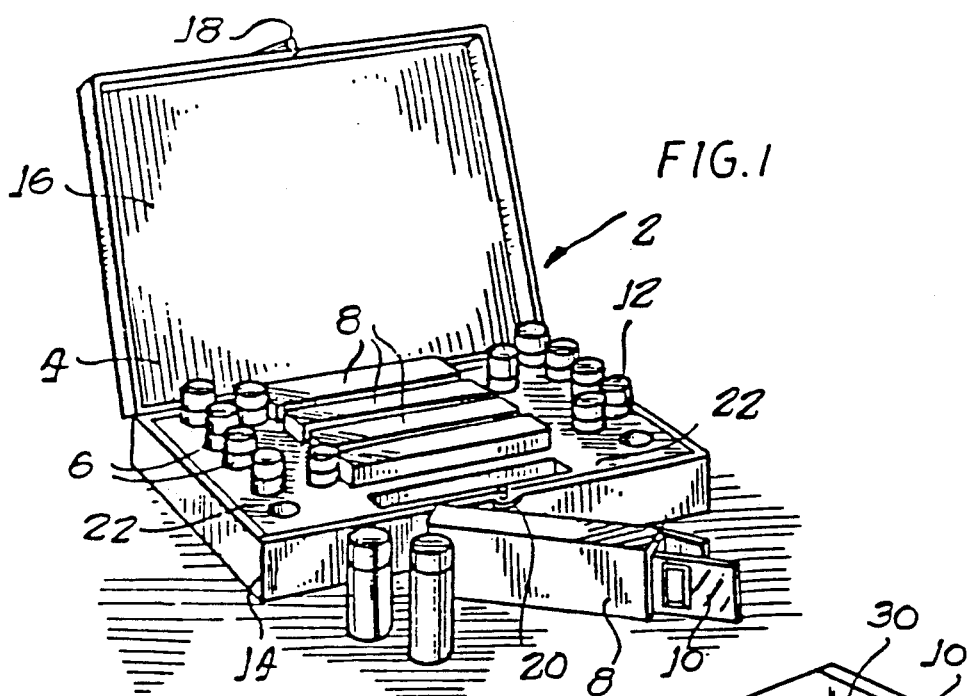
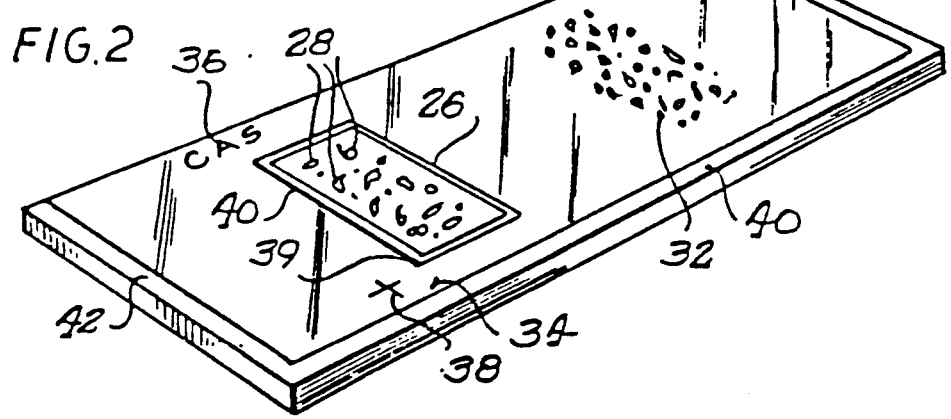
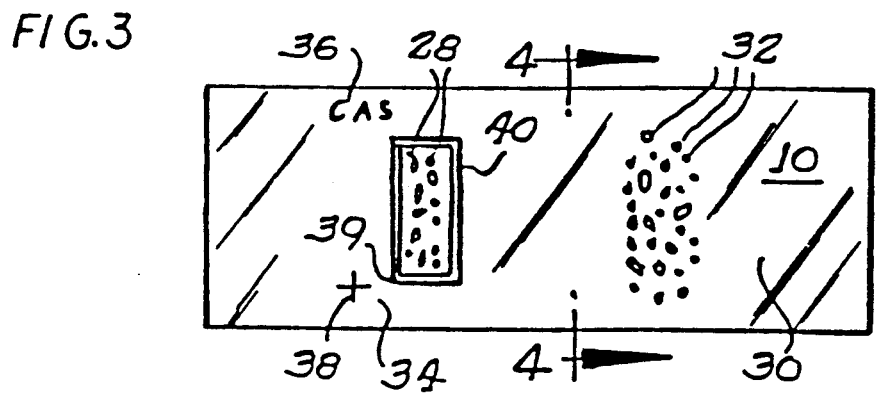
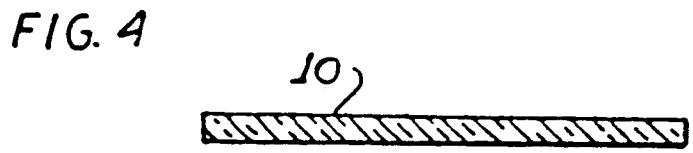

FIG. 5
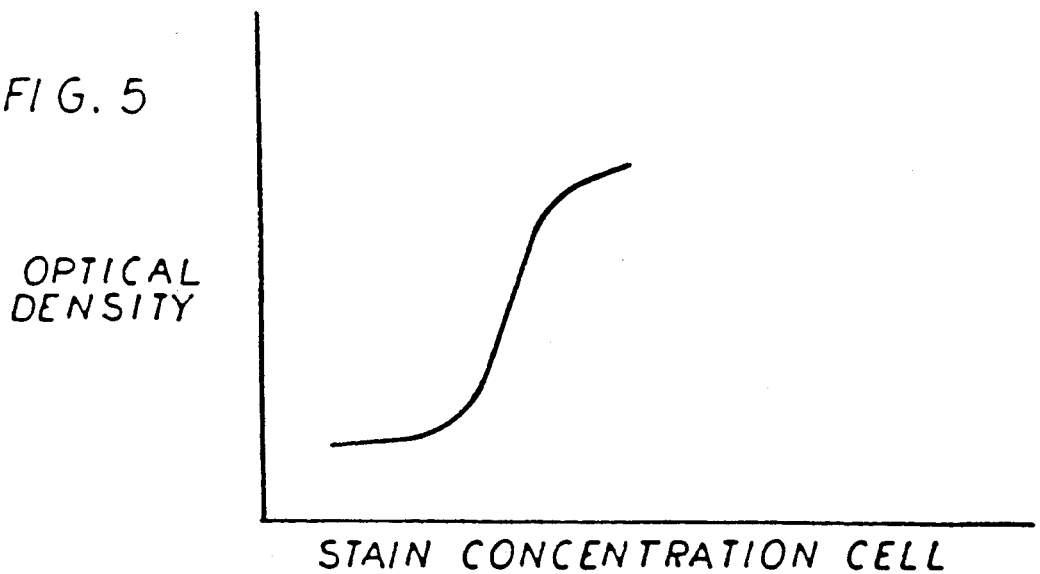
FIG.6
DNA PLOIDY ANALYSIS
CONTROL CELL PLOIDY CALIBRATION
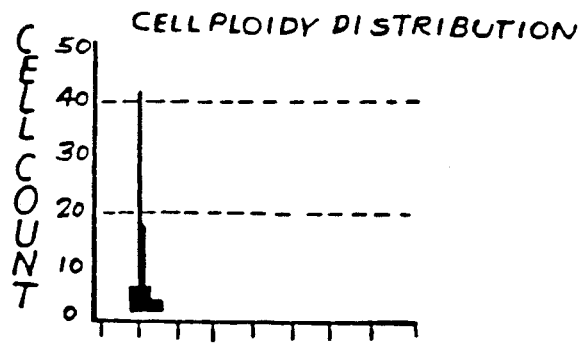
FIG.7
PATIENT NAME
ACCOUNT NUMBER
PATHOLOGIST
CELL PLOIDY DISTRIBUTION
SUMMARY STATISTICS
| | |
|---|---|
| CELL TYPES | CN 12 |
| STATISTIC 1 | 13.24 |
| STATISTIC 2 | 0.0056 |
| STATISTIC 3 | 1345.0 |
| ICV PEAK 1 | 0.2318 |
| ICV PEAK 2 | 0.6581 |
DNA CONTENT (PICOGRAMS)

APPARATUS AND METHOD FOR ANALYSES OF BIOLOGICAL SPECIMENS

This is a continuation-in-part application of application Ser. No. PCT/US86/02411 filed Nov. 4, 1986, which became U.S. application Ser. No. 76,685 filed Jul. 2, 1987, now abandoned, which PCT application was a continuation-in-part application of application Ser. No. 794,937 filed Nov. 4, 1985 now U.S. Pat. No. 4,741,043.

This invention relates to a method and apparatus for clinically testing and quantifying biological specimens such as cells through image analysis of the specimens.

BACKGROUND OF THE INVENTION

The present invention is directed to a quantitative testing apparatus and method which may be used for a wide range of diagnostic testing and evaluation of various cells, tissues, or other materials taken from the human body. The present invention is directed to an apparatus (hereinafter the "kit") and method used in image analysis using pattern recognition techniques to analyze and quantify cell constituents or components which may be stained. This kit and method are particularly useful and adaptable to the method and apparatus disclosed in application Ser. No. 794,937 filed Nov. 4, 1985, now U.S. Pat. No. 4,741,043 which is fully incorporated by reference herein. In a preferred embodiment the method and the kit may be used in the measurement of cellular DNA for the purpose of cancer diagnosis and prognosis.

As will be explained in greater detail, the present invention is directed to providing equipment of a user interactive nature for use not only by researchers, but also by a pathologist in a laboratory and to low-cost equipment which can be acquired by a typical pathologist laboratory.

The current state of the art in pathology laboratory is to estimate the content of cell constituents or components (hereinafter "cell objects") such as constituents or components of DNA by the visual observation of the pathologist who observes primarily the shape and texture of the cell objects after staining. For example, in connection with suspected cancer cells the pathologist observes the shape and texture of the cell objects and then classifies them into a normal category or into one of several abnormal cancer categories. These evaluations, however, are very subjective and can not differentiate and quantify small changes in DNA within individual cells or in very small populations of abnormal cells, which changes have clinical significance in the diagnosis and prognosis of cancer as discussed infra. Although there are commercially available general purpose flow cytometers, which are very expensive units and which can handle liquid blood specimens or tissue disaggregations, these cytometers are incapable of working on standard tissue sections and of using microscope slides which are the preferred specimen forms used in pathology laboratories. Additionally, an image analysis technique allows analysis of morphological features of cells such texture, in combination with size and shape of cell nuclei and alterations in nuclear-to-cytoplasmic ratios of cells whereas the flow cytometer does not allow such analysis.

The progression of the skill-of-the-art techniques for testing in anatomy, surgery, and histopathology has to date evolved to a primarily visual comparison of stain enhanced cells and tissues to human memory of previous examples. New advances in measurement, (i.e., the application Ser. No. 794,937) to quantify and replace these current state-of-the-art subjective comparisons to past memory, require calibration of the measurement instruments. Novel calibration means are required, e.g., as compared to chemical analysis calibration (where the state-of-the-art for calibrated measurement is well developed), because the material, although it is being read by light transmission measurements as in chemical analysis, is actually presented to the measurement instrument as a thin solid material, preserving cell and tissue morphology, on a transparent substrate. Methods, and the state-of-the-art techniques for calibrating such readings after suitable quantitative staining for specific cell or tissue parts, are essentially undeveloped and non-existent. Adequate calibration, such as described in this invention, will revolutionize and transform testing in these laboratories from subjective to objective. Such calibration preferably is on a test-by-test basis, i.e., on the individual microscope slide for each specimen, because the tested objects are so incredibly small, e.g., measuring picograms of DNA in cells with nuclei on the order of 100 micrometers$^2$ in size, that very small shifts in light transmission or subtle staining variations make the measurement process too error prone without such calibration.

The use of image analysis generally requires staining cell objects on a microscopic slide. The use of image analysis techniques and equipment and stained specimens by pathologists in a conventional pathology laboratory involves solving a number of problems, including variation of stain, variation of optical densities of stained cell objects and calibration of microscopic slides with stained objects thereon, all of which have been overcome by the present invention. There are a number of available staining techniques which can be used. The Feulgen staining technique may be used to stain DNA in cell objects with dyes, for example, with thionin, Azure A, Azure C, pararosanilin and methylene blue. Proteins may be stained with congo red, eosin, an eosin/hematoxylin combination, or fast green. Enzymes may be made visible with diaminobenzidine or 3-amino-9 ethylcarbazole or alkaline phosphatase in combination with a dye substrate; cell organelles may be stained with methylene blue; and ribosomes with methylene blue and mitochrondia with giemsa stain. For purposes of this application "stain" includes an enzyme (such as alkaline phosphatase) in combination with a dye substrate to make something visible. Moreover, as used herein, stain includes counter stains such as methyl green. In breast cell cancer analysis some of these stains are used in combination with monoclonal antibodies which detect estrogen or progesterone receptors. Antigen analysis may include the steps of binding of monoclonal antibodies to the specimen and control cell objects. Later the monoclonal antibody may be conjugated with an enzyme stain. Also, the monoclonal antibody may be conjugated with a fluorescent material or stain. Then the fluorescent stain may be excited at a wave length to induce the fluorescence and then this may be observed at another wave length at which fluorescent emission occurs. When the antibody is made for a particular virus, the control cell specimen objects may be treated with a nucleic acid probe specific for the genome of the virus.

Variation in the degree of staining of cell objects and the variation of the optical density of the stained cell objects presents a problem in the quantitation of the stained cell objects through image analysis. The staining of cell objects, such as the DNA with Azure A, will vary substantially not only from slide to slide or from batch to batch by the same pathologist, but will vary substantially between different pathologists and different laboratories. Because the image analysis equipment is measuring grey level or optical densities and because it is desired to provide a true actual amount of DNA per cell in picograms from optical density measurements from stained cell objects, it is important to overcome the problem of different staining factors for different specimens. Also, image analysis techniques use microscopes and optical lighting which are adjustable to provide different intensities of light when used by the pathologist. Trained researchers, in research laboratories may be equipped to adjust the optical intensity to the desired conditions for image analysis by image pattern techniques, but this generally will not be accomplished with the precision necessary in the usual pathology laboratory. Thus, there is a need to overcome the problem of this optical density and staining variable.

Heretofore in cell analysis, an inexpensive and simple quantitation of cell objects has not been available. For example, except for those using only more expensive and sophisticated equipment, relative comparisons of data which are a function of cell object content have been only available to workers studying the proliferation of cell objects. In the case of DNA, absolute values of DNA content of cell nuclei in terms of picograms has not been readily available to laboratory workers for uses such as cell cycle analysis. Moreover in connection with DNA, this is clinically significant in the diagnosis and prognosis of cancer. The analysis of the DNA content of cells has been shown to be of value in the assessment of proliferations of benign and malignant cells. Abnormal DNA content (aneuploidy) has been observed consistently in numerous cancers such as prostate, colon, cervical, breast, and bladder. Also, preliminary data indicates that assessment of aneuploidy has prognostic value. See Atkin, Cytophotometric DNA Determination Corrrelated to Karyotype, Particularly Cancer, The International Academy of Cytology Analytical and Quantitative Cytology and Histology: 9:96-104 (1987). In addition the presence of an increased number of cells which are synthesizing DNA (so called "S phase" cells) has been shown to relate the extent of tumor cell proliferation, in some cases.

The method and kit of this invention coupled with any apparatus of carrying out image analysis of cell objects after staining, using pattern recognition techniques (such as the apparatus disclosed in Ser. No. 794,937, filed Nov. 4, 1985), permit a worker to readily and inexpensively not only detect minute alterations in cell objects including DNA, but also to measure and quantify the amount of cell objects as an aid to statistical analysis in research and patient diagnosis and treatment.

The present invention overcomes the problem of high costs heretofore associated with computerized equipment used for image analysis; and to this end, the present invention is an interactive system in which the pathologist performs a number of tasks including the selection, preparation, placement and staining of cells on microscopic slides. The pathologist is provided with the kit of the invention which includes stain and slides both of which are especially prepared and calibrated. The slide includes reference cells to aid in the diagnosis of the specimen cell objects and to assist in overcoming the staining density problem above-described. The present invention also permits location of cell objects for examination as to their morphology and preserves their location for a later analysis or corroborating analysis by a second pathologist when so desired. With respect to nuclei, measurements may be obtained as to area in microns, total nuclear optical density or nuclear mass in picograms, average nuclear optical density, nuclear texture, and deviation of the nuclear shape from being a round nucleus. Also, a number of such measurements may be made of the cell cytoplasm.

When the kit of this invention is used for cell analysis, tissue and cell specimens are applied to a slide which then is stained with a specific stain that combines proportionately with the cell objects which generally essentially renders invisible the remainder of the cell so that the image analysis measures the cell object content such as DNA which is concentrated principally at the nucleus of the cell. The stain associates with the cell object to provide a detailed nuclear structure and pattern which may be visually observed and interpreted by the pathologist using an apparatus for image analysis. In connection with DNA analyses for diagnosis and prognosis of cancer, the amount of DNA in the malignant cells generally is substantially greater than that for normal cells because the malignant cells usually are dividing and replicating rapidly or the malignant cells have abnormal numbers of chromosomes or have defective chromosomes.

The kit of the invention comprises a microscopic slide which includes a reference area and a specimen cell object area for receipt of specimen cells. The reference area contains a reference means for simultaneous staining for a predetermined time with the specimen cells or cell objects after the specimen cells or cell objects are applied to the specimen cell object area of the slide. According to the invention this simultaneous staining of the reference means and specimen cell objects with a stain of predetermined concentration permits a self-calibration of the slide as hereinafter described. The kit also includes one or more containers of stain and may include a container of rinse sulfonating agent for addition to a rinse used in preparation of the slide for microscopic image analysis. The amount of stain in the kit affects the optical density of the reference means and the specimen cell objects. This is an important aspect of the invention. After the staining the optical density of the reference means (and the specimen cell objects if they contain the material being investigated and measured such as DNA) will be a linear function of stain concentration per unit of material (such as stain concentration per cell object if the material being stained are cells) only over a select range of stain concentrations per stained cell object such that an optical density in the range of from about 0.1 to 0.8 is provided. Except for this linear portion, a curve of a plot of optical density versus stain concentration per cell will not be linear and/or not provide readily measurable or understood differences in optical densities with changes in stain concentrations per cell object. This is important to cell analysis. In cancer diagnosis and prognosis observation of varying DNA content by virtue of differing stain content and the resulting differing optical densities will be more readily detected and understood if the variation of optical density to stain concentration per cell is linear and the optical density is in the range of from about 0.1 to about 0.8. Quantitation of DNA, however, is only an example and analysis of any cell object by optical density and will be more readily understood if the optical density of the cell object is linear. Hence it is important that the stain in the kit be provided in an effective amount of stain to provide an optical density to the reference means after staining or a predetermined amount of time such that the optical density of the reference means will be a substantially linear function of the stain concentration of the reference means after staining and the optical density is in the range as aforesaid. The same is true of the specimen cell object if the object contains the material being referenced by the reference material.

The reference means for staining contains or constitutes any reference material which combines with stain proportionately to the combination of stain with the cell objects being analyzed. In connection with DNA analysis, the reference material may be rat liver nuclei, trout erythrocytes, chicken erythrocytes, dried DNA or cultured cell lines which reproduce themselves such as lymphoblastoid cells. In connection with proteins or enzymes the reference material may be any material containing a known amount of protein or enzymes to which an analysis is being directed.

The stain of the kit also may include a stain sulfonating agent. The stain sulfonating agent and rinse sulfonating agent are used in conjunction with acidic aqueous solutions of stain and rinse. Preparation of the slide frequently contemplates putting the stain in an acidic aqueous solution and then staining the reference means as well a the specimen cell objects with the aqueous stain solution. After the materials on the slide are stained, they are rinsed with a solution which also frequently is an acidic aqueous solution. In such cases consistent reproducible results demand stains and rinses having pHs within consistent relatively narrow ranges. A sulfonating agent which is compatible with the stain aids in binding the thionin or Azure A to the hydrolyzed DNA.

In an alternate embodiment of the invention, the microscopic slide of the kit includes an optical density reference area which area includes a material which has a predetermined known optical density to calibrate the microscopic slide with the instrument being used to study the specimen cell objects. Without the optical density reference area, the slide in conjunction with the kit described herein is self calibrating without regard to certain other variables that may change from analysis to analysis. These include variations in thickness and type of glass used in the slide as well as variations in temperature and humidity conditions encountered during analysis and which could affect analysis.

The method of the invention permits the quantitation of specimen cell objects by comparing the optical density of the stained specimen cell objects with the optical density of the stained reference material having known amounts of material to be quantified. For example, in connection with DNA quantitation, trout erythrocytes are known to have 5.6 picograms of DNA. Use of these cells as a reference material will permit the calculation of the DNA content of specimen cell objects in terms of absolute DNA weight when such specimen cell objects are simultaneously prepared and stained and the optical densities of the stained reference material and specimen cell objects are compared. This calculation and computer program relative thereto are described in my application Ser. No. PCT/US861/02409 filed Nov. 4, 1986 which application is fully incorporated herein. In breast cell analysis for the quantitation of estrogen receptors cultured breast cancer cells or tissue sections of organic material e.g. endometrium may be used as reference cells and as a source of reference cell objects.

In connection with the quantitation of nuclear DNA, the method of the invention includes providing a slide with a reference area and a specimen cell object area; providing a reference material in the reference area, the reference material having physical characteristics which include a known amount of DNA and permit association of the reference material with a stain which is proportional to an association of the stain with DNA; providing specimen cell objects in the specimen cell object area; simultaneously staining the reference material and the specimen cell objects with a stain in aqueous solution of stain for a predetermined amount of time, the stain in aqueous solution being in an effective amount to provide the reference material with an optical density after staining which will be a substantially linear function of stain concentration of the reference material; measuring the optical density of the reference materials after staining; measuring the optical density of the specimen cell objects after staining; and determining the quantitative amount of DNA in the specimen cell objects from the measured optical densities.

A very important alternate embodiment of the invention is rat liver cells nuclei as a reference means in conjunction with thionin stain. Rat liver has tetraploid cells having 13.4 picograms of DNA which give a number of measuring points for DNA content as well as diploid cells having 6.7 picograms of DNA. With tetraploid cells, rat liver tissue is advantageous over trout erythrocytes or other reference materials which include only large amounts of diploid cells, and hence, have fewer measuring points for DNA. After staining, the larger amounts of DNA in the rat liver nuclei, and the larger size of these nuclei, provide a reference material with an increased optical density. Larger size, more DNA and increased total optical density permits more precise calibration and thus less measuring error. Moreover, rat liver cells not only look substantially like human tissue, they combine with stain similar to the way human tissue combines with stain. This similarity results in similar optical densities for simultaneously stained human and rat tissue. Finally, rat liver tissue are readily cut, sectioned and applied to microscopic slides to provide a sample with an even distribution of cells which are oriented such that staining and observation are facilitated.

Thionin is important to the alternate embodiment and use of rat liver cells as a reference because it is very selective in staining DNA. Many other commercial stains such as Azure A often have impurities which will stain other material in a cell such as proteins. This is deleterious to the process of the invention because the relationship of optical density and the amount of DNA will not be as precise as with a pure stain which is precisely selective in staining DNA.

The kit and method of the invention permits an easy and inexpensive detection of minute alterations in specimen cell objects. In connection with cell object alterations in DNA content, this is done by providing a real and accurate measurement of the DNA in picograms. The invention also permits measurement and quantification of the amount of DNA and relates it to stored statistical analyses to aid in the diagnosis. More specifically, the invention in conjunction with my inventions disclosed and described in my applications Ser. No. 794,937 filed Nov. 4, 1985 and Ser. No. PCT/US86/02409 filed Nov. 4, 1986 in respect to DNA analysis allows an iterative analysis of specimen population cells and provides a histogram or display of the population distribution of the cells with respect to their DNA content and with respect to a standard DNA for normal cells so that subtle shifts in population distribution can be readily understood. To this end cell nuclei images are not only acquired and stored but the data therefrom can be integrated with statistical data to provide multi-variate analysis, discrimination of cells, histograms, and scattergrams of cells or cell populations.

Accordingly, a general object of the invention is to provide a new and improved apparatus and method for analyzing cells or other biological materials by using image analysis techniques.

A further object of the invention is to provide a new and improved kit which includes a stain and a slide or support for specimen cell objects which slide has a reference means or cell objects thereon wherein the stain with the slide permits calibration of the slide for image analysis of the slide in conjunction with image analysis equipment.

Another object of the invention is to provide a new and improved apparatus and method for making a ploidy analysis of cells using image pattern recognition equipment.

These and other objects and advantages of the invention will become apparent from the following description taken in connection with the accompanying drawings.

DETAILED DESCRIPTION OF THE DRAWINGS

FIG. 1 is a perspective view of a kit in accordance with the invention.

FIG. 2 is a view of a specimen slide or support constructed in accordance with the invention.

FIG. 3 is a plan view of a slide with materials thereon for control cells, specimen cells, light calibration, reference location, and integrity checking.

FIG. 4 is a cross sectional view taken along the line 3—3 in FIG. 3.

FIG. 5 is a post staining schematic plot of optical density versus stain concentration per cell.

FIG. 6 is a histogram of control cell ploidy calibration made in accordance with the invention.

FIG. 7 is a histogram of a summary report of cell ploidy distribution in accordance with the invention.

DETAILED DESCRIPTION OF THE PREFERRED EMBODIMENTS

As shown in the drawings for purposes of illustration, the kit and method of the invention will generally be used in conjunction with an apparatus for automatically analyzing "cell objects". The latter term is used herein to be generic to cells, including but not limited to blood cells or cells taken from tumors, or the like, which are prepared so that their nuclei may be observed. In the case of the quantitation of DNA, the cells are prepared using a Feulgen staining reaction such that DNA in the cell nuclei may be observed. Hydrochloric acid hydrolyzes ribose—nucleic acid bonds to the DNA to give aldehyde sugar residues. A stain such as thionin or Azure A then couples via the Schiff reaction to the sugar aldehydes to give a blue-violet color. Other Schiff type reagent stains which may be used in the invention include thionin, Azure C, pararosanilin and acriflavine. Other stains which may be used in the invention which are not Schiff type reagent stains include methyl green, ethyl green, methylene blue, hematoxylin, acridine orange and giesma. Moreover, the present invention is not only useful for the staining study of DNA for ploidy analysis and blood cell analysis, but also can be used to analyze pap smear cells, monoclonal antibodies conjugated to stains and used as cell markers, and other infectious diseases which can be diagnosed by DNA probes for viruses; and as previously stated, can be used for the study and quantitation of proteins, enzymes, cell organelles, ribosomes and mitochrondia stained with a compatible stain and rinse.

As shown in FIG. 1, the kit 2 includes a container 4 comprising one or more bottles or vials of stain material 6, one or more boxes 8 of microscopic slides 10 and one or more bottles or vials of rinse sulfonating agent 12. The container has a base 14, lid 16 hinged to the base and a latch which includes latch members 18 and 20 which frictionally and snappingly engage the lid and base respectively to close the container. The base of the container has a cushion 22 of sponge, foam or the like with molded or cut inserts 24. The inserts have the shape of the vials or boxes of slides and are adapted to hold the bottles and boxes in a fixed position without damage during transport of the kit.

Turning now to FIG. 2, the microscopic or specimens slide 10 may be of any size or shape, but because of the familiarity of lab technicians and pathologists with glass slides used with microscopes, it is preferred that a slide 10 be an actual microscope slide of glass which typically measures 3 inch by 1 inch. The illustrated slide 10 shown in FIG. 2 has a preprinted border 26 which defines a reference area within which are located the reference means for staining such as reference cell objects 28. The reference means in this illustrated embodiment of the invention, are rat liver cells, of known size and shape and DNA content, which is about 6.7 picograms of DNA for diploid cells and 13.4 picograms of DNA for tetraploid cells. The reference cell objects may be other types of cells having dark centers or nuclei which stain well, such as trout erythrocytes, i.e. trout red blood cells having a DNA content of 5.6 picograms, chicken erythrocytes, i.e. chicken blood cells having a DNA content of 2.51 picograms; they may be artifacts deposited on the slide, which may or may not have cell shapes, or the cell objects 28 may be well known plastic beads of a predetermined size which will react with a particular fluorescent stain or enzyme stain. The reference cell objects will vary from test to test and the present invention is not limited to any particular test or cell objects therefor.

The slide also includes a specimen cell object area 30 for receipt of specimen cell objects 32 which are, in this instance, cells from a slice of tissue (such a tumor tissue), or a needle aspirate of tumor tissue or monolayer of blood cells or other cells, at the area 30 on the slide.

In the preferred embodiment of the invention, the slide also includes an optical density reference area which preferably is a printed mark such as a cross 34 on the slide. This area has a material with a predetermined known optical density which can be used as a reference to calibrate an instrument analyzing the slide. As will be explained in greater detail hereinafter, a histogram and instructions are provided to the operator from an instruction control logic to the operator as described in my application Ser. No. 794,937 filed Nov. 4, 1985 and the operator manually adjusts the optical light intensity until the desired intensity is obtained for the optical density reference material, and the background light.

The system logic as described in my application Ser. No. 794,937 also is calibrated with the optical density reference material to read the proper optical density of objects.

The slide also may include an optical integrity pattern 36 as a safeguard to the integrity of the system. This pattern provides an integrity check or identification from the slide 10 by analyzing a predetermined and prefixed optical pattern on the slide which is read and measured as to gray levels and physical dimensions before the analyzing may be begun. Herein, the optical integrity pattern may be in the form of initials CAS located above the control cell objects as seen in FIG. 2. Manifestly, the integrity check may be the cross 34 of the optical end or any other material on the slide 10.

The kit and slide is useful for later analysis of the specimen cell objects 32 on the slide 10; and to aid in the recall of cell images stored in memory or to allow the operator or another person to return to a given cell for a second review thereof at a later time. To this end after the slide 10 has been secured on a microscope stage, a certain location on the slide, such as the center 38 of the cross 34, is noted as the zero-zero X-Y reference point; then the location registers for the X and Y distances are zeroed at this point so that subsequently all cell locations may have a specific X and Y coordinate address from the center 38 of the cross. A further easy location to find with the adjustment with the microscope stage is a corner such as the right hand lower corner 39 of the box border 40 within which are located the reference cell objects 28. Herein, the box border 40 is printed on the slide and it also may be used for optical density calibration rather than the special cross 34. On the other hand, by suitable logic and control, any point on the slide and microscope stage at which the classification operation begins may be taken as the zero X and Y location with the location registers for the X and Y coordinates being zeroed initially at this location and then providing a readout for each cell location from this zeroed location.

The slide may further include locator strips on the slide to facilitate location of specific cell objects. The particular X and Y location for each specimen cell may be obtained by the use of conventional stepping motor techniques which are well known in the art and which are relatively expensive. In a preferred embodiment of the slide the X and Y locations are easily determined for any given location with an X direction sensing strip 40 which may be fastened to the underside of the microscope slide 10 for movement with the slide past a sensing read head secured to a stationary part of the microscope and which reads a sensing scale on the sensing strip and provides a digital output to an interface electronic which provides the X coordinate in digital numbers to an instrument control logic for storing in memory and for display. Likewise, a similar strip 42 is fastened to the slide for movement in the Y direction with the stage past a read head which is secured to a stationary part of the microscope so that the read head may read the indicia on the Y strip 42 to provide a digital readout to the interface electronic which supplies digital signals to the instrument control logic for storage of the Y coordinate and for showing the Y coordinate on the video monitor adjacent the X coordinate. The system can be reversed with the read heads fastened to the stage for movement therewith with the scale strips 40 and 42 being mounted stationary to provide digital readouts as the heads move thereacross. The illustrated and preferred strips and heads commonly used as instrument feelers gages, or the like, sold under the trademark "SYLVAC" using magnetic strips and magnetic read heads.

The stain material contained in the bottles 6 of the kit includes stain and may include a sulfonating agent. The stain is not only compatible with the specimen cell objects and reference cell objects, but is an amount effective for providing an optical density to the reference cell objects and specimen cell objects upon application of an aqueous solution of the stain for a predetermined time which optical density is substantially a linear function of stain concentration per stained reference cell object. As shown in FIG. 5, after cell objects are stained with an aqueous solution of stain, a curve of a plot of optical density versus stain concentration stain per stained cell object is substantially linear as at 46 over a select range of stain concentration per cell. Prior to use the stain is generally mixed with 0.1N HCl aqueous solution water and then applied to the cell objects under study for a predetermined amount of time. Thereafter the slide is rinsed and studied. Keeping the amount of stain after it is mixed with water such that for a given staining time range the staining solution provides the concentration of stain associated with the cell objects along the substantially linear portion of the curve of FIG. 5 is an important aspect of the invention. Keeping the stain concentration per stained cell object a substantially linear function of optical density facilitates a determination of stain concentration per stained cell object from optical density generally will facilitate the measurement of optical densities and differences in optical densities over relatively small differences in stain concentration per cell object. These factors are important in quantitation of cell constituents or components from stain concentration which is in turn measured by optical density. In the case of thionin and the quantitation of DNA, the concentration of stain in the aqueous staining solution is in the range of from about 1 to about 5 mg/ml for a staining time in the range of from about 60 to 120 minutes, the concentration of the stain preferably being about 2 mg/ml for a staining time of about 60 minutes. In the case of Azure A and the quantitation of DNA, the concentration of stain in the aqueous staining solution is in the range of from about 4.9 to about 5.1 mg/ml for a staining time in the range of from about 115 to 120 minutes, the concentration of the stain preferably being about 5 mg/ml for a staining time of about 120 minutes.

The aqueous solution of thionin or Azure A stain applied to the slide will be acidic. In the case of staining DNA with these stains, the aqueous solution of stain has a pH of 2.7 controlled with 0.1N hydrochloric acid. The aqueous solution of stain also may include a stain sulfonating agent at a concentration in the range of from about 2 to 16 mg/ml, the concentration preferably 8 mg/ml.

Frequently after cell objects on the slide are stained such as with an acidic aqueous stain solution, excess stain is rinsed therefrom with an acidic aqueous rinse solution. In the case of staining DNA with thionin or Azure A and thereafter rinsing it, the aqueous rinse solution is preferably controlled with 0.05N hydrochloric acid to a pH of about 2.65. The rinse solution will also contain a rinse sulfonating agent in an amount in a range of from about 3 to 6 mg/ml and preferably 5 mg/ml.

In a preferred form of the invention the slide box includes a base 48 and lid 50, each slide box containing five microscopic slides maintained in juxtaposition in side-by-side spaced relation. Longitudinal ribs run the length of the two opposite sides of slide box base to maintain the slides in their position within the box. The ribs are separated sufficiently to permit the microscopic slides to slide therebetween and be held by the ribs at the longitudinal edges of the slides such that the slides are in juxtaposition. An aperture 52 in the lid permits the aspiration of stain into a closed box by a hypodermic needle or the like such that the box may be used for application of stain to the slides in lieu of coplin jars.

In connection with the analysis of DNA with thionin, a kit in the preferred embodiment includes seven vials each containing 200 mg of thionin (Certified) with 0.8 g of $K_2S_2O_5$ stain sulfonating agent. Each vial is sufficient for preparation of 100 ml of thionin aqueous solution to provide a concentration of 2 mg/ml of thionin, as hereinafter described. The kit also includes seven vials of rinse sulfonating agent which is 1.5 g of $K_2S_2O_5$ (an equal molar amount of $Na_2S_2O_5$ may be used in lieu of the potassium salt) and five boxes of slides. Each vial of rinse sulfonating agent when the $K_2S_2O_5$ is mixed with water and hydrochloric acid is sufficient to make 300 ml of rinse reagent solution. The five boxes are containers each with five microscopic slides include DNA reference cell objects which are rat liver cells.

The kit with thionin may further include a bottle for the aqueous stain solution marked to indicate 100 ml of volume for preparation of the aqueous acidic thionin solution; and a bottle for rinse solution marked to a volume 300 ml for preparation of 300 ml of acidic rinse solution. Materials used with the kit and method of the invention, but not necessarily supplied with the kit, include 0.05N HCl, 0.1N HCl, 5N HCl and eleven 75 ml coplin jars.

In connection with the analysis of DNA with Azure A, a kit in the preferred embodiment includes seven vials each containing 375 mg of Azure A (Certified) with 1.5 g of $K_2S_2O_5$ (an equal molar amount of $Na_2S_2O_5$ may also be used in lieu of the potassium salt) stain sulfonating agent. Each vial is sufficient for preparation of 75 ml of Azure A aqueous solution to provide a concentration of 5 mg/ml of Azure A, as hereinafter described. The kit also includes seven vials of rinse sulfonating agent which is 1.5 g of $K_2S_2O_5$ and five boxes of slides. Each vial of rinse sulfonating agent when the $K_2S_2O_5$ is mixed with water and hydrochloric acid is sufficient to make 300 ml of rinse reagent solution. The five boxes or containers each with five microscopic slides include DNA reference cell objects which are trout red blood cells.

The Azure A kit may further include a bottle for the aqueous stain solution marked to indicate 75 ml of volume for preparation of the aqueous acidic Azure A solution; and a bottle for rinse solution marked to a volume 300 ml for preparation of 300 ml of acidic rinse solution. Materials used with the kit and method of the invention, but not necessarily supplied with the kit, include 0.05N HCl, 5N HCl, 0.1N HCl and eleven 75 ml coplin jars.

According to the invention in respect to quantitation of DNA using the Feulgen staining reaction, preparation of the slides using the kit preferably is as follows.

Cytologic specimens (e.g. cytospin preparations, touch preparations, fine needle aspirates, smears and smear preparations) are air dried for about 30 minutes to about 2 hours and fixed in 10% neutral buffered formalin for about 30 minutes. Then the slides are rinsed in deionized water for about 5 minutes and air dried. The formalin fixed, air dried slides may be stored at room temperature until stained.

The aqueous thionin solution is prepared from the kit by transferring the entire contents of one stain reagent vial into one thionin solution bottle marked to a volume of 100 ml. The bottle is filled to the line with 0.1N hydrochloric acid, closed tightly and stirred. The bottle is kept closed tightly and stirred for one hour at room temperature (18°–20° C.). Then the solution is filtered to eliminate stain which has not dissolved.

The acid aqueous rinse solution is prepared by transferring the entire contents (1.5 g of $K_2S_2O_5$) of one rinse sulfonating agent vial into a rinse bottle marked to a volume of 300 ml. The rinse bottle marked to 300 ml is filled to the mark with 0.05N hydrochloric acid. The container is closed tightly and mixed until the rinse buffer is completely dissolved. Both aqueous thionin and rinse solutions are stable for 4 to 6 hours when stored at room temperature (18° to 28° C.). Both the thionin and rinse solutions can be used for staining up to 2 sets of slides or ten slides providing the second set is completed within 6 hours from when the solutions were made. A similar procedure is used with the Azure A kit to prepare that stain for use in preparation of staining slides.

Further an acid hydrolysis solution (75 ml) which is 5N hydrochloric acid solution is prepared for preparation of the cell objects via a hydrolysis reaction of the DNA as described above. This 5N hydrochloric acid solution has a pH of 0.5.

The slides are stained and prepared with the thionin kit according to the following procedure although the same procedures may be used with the Azure A kit.

For Cytologic Material

1. The slides are fixed in 10% by volume formalin adjusted to a pH in the range of from about 7.2 to about 7.5 for 30 minutes at room temperature.

2. The slides are placed in a coplin jar containing 5N hydrochloric acid for about 60 to about 75 minutes.

3. The slides are transferred from the coplin jar containing the hydrochloric acid solution directly to a coplin jar containing thionin solution and stain for about 1 hour.

4. Three coplin jars, each filled with the rinse solution are ready for use. The slides are placed into the first coplin jar containing rinse solution and permitted to contact the rinse for about 30 seconds. The slides then are moved to the second coplin jar filled with rinse solution and are permitted to stand for about 5 minutes. The slides are then moved to the third coplin jar filled with rinse solution and again are permitted to stand for about 10 minutes.

5. The slides then are washed for about 5 minutes in running distilled water.

6. The slides are put in acid alcohol (0.37% hydrochloric acid, 70% ethanol) for 5 minutes.

7. The slides are dehydrated in absolute ethanol for about 5 minutes to prepare slides for coverslipping.

8. The slides are cleared in xylene for about 5 minutes.

9. The slides are mounted with a synthetic resin and a coverslip.

The presence of dark blue staining in the nuclei of the control cells in the calibration area of the slide is evidence of proper performance of the reagents. The Feulgen reaction will produce specific blue staining of nuclear DNA. Nucleoli, if present, and cytoplasm should show no staining. Normal human cells have a DNA content equal to 93% of the amount found in the reference cell objects in the reference cell object area, i.e. 6.7 picograms. Malignant cells may show normal, increased, or occasionally decreased amounts of DNA. Proliferating (S phase) cells show increased amounts of DNA compared to the main DNA peak for that cell type.

After calibration of the apparatus disclosed in the application Ser. No. 794,937 for optical density with the optical density reference area of the image analysis apparatus, in respect to a slide prepared in the above described procedure, a control program logic requests a reference cell object calibration function as shown in the histogram of FIG. 6. During this control cell calibration, the operator moves the microscope slide to shift the reference cell objects 28 into view on a monitoring screen. When an individual stained reference cell object 28 is within a reference area the summed optical density for that stained reference cell object is measured and stored. After a suitable number of stained reference cell objects have been analyzed, an analyst will be provided with a histogram such as shown in FIG. 7 such as on a video monitor which shows an analyst the control cell object ploidy distribution as having a relative quantity of DNA. Internally within an instrument control logic, as described in my application Ser. No. PCT/US86/02409 filed of even date, the modal value of the histogram of individually summed optical density values actually measured for the control cell objects are compared to a predetermined standard or reference amount of DNA which the control cells are known to have. The actual summed optical density found by the operator is divided into the stored reference DNA value to provide a factor by which to adjust for the internal reference level has been set up.

The analyst may now begin cell data acquisition for the DNA ploidy analysis. The analyst will select a number of field locations along the specimen cell object area 30 for analysis. The analyst will move the microscope slide to move into view specimen cell objects to be analyzed for DNA content as well as for cell morphology if desired. The analyst will classify the cell in a manner similar to that disclosed in the application Ser. No. PCT/US86/02409 and in U.S. Pat. No. 4,453,266 to give summed optical density for the specimen cell object i.e., a stained cell object nucleus, as well as its area, its roundness, and other classification information. A histogram may then be provided which provides DNA content. Generally the analyst will select a number of cell objects in each field or area and then will move the microscope stage to position a number of different fields of specimen cell objects into view and to take and analyze a number of these specimen cell objects until he feels he has a representative sample. This permits the making of a histogram, such as shown in FIG. 7 which shows the number of cells of a particular DNA content and shows the DNA content averages for each of the reference peaks. The data may also be stored internally within a computer logic for later recall and comparison with data of any new specimen from the same patient for analysis of the patient's progress or regression.

After staining and image analysis of the stained slides, the control cells should give a single main peak indicating the relative position of the DNA content of normal human cells. Shifts of the main DNA peak on unknown samples indicate an abnormal DNA content. Skewing of the main peak to the right especially with production of a second peak with 2 times the DNA content of the first peak indicates a proliferating cell population. 50-100 cells should be counted for non-proliferating populations and 100-200 randomly chosen cells for proliferating populations for reasonable accuracy.

The present invention is not limited to the above described embodiments but extends to cover other embodiments, not shown or described, but falling with the ambit of the appended claims. For example, cell objects may be stained with methyl green to counterstain for diaminobenzidine (DAB) so that nuclei may be first isolated by specific wavelengths of light by imaging techniques; and, then the monoclonal antibody conjugated with DAB may be shown up by a second wavelength of light imaging techniques.

What is claimed is:

1. A kit for the quantitation of cell nuclei comprising:
a microscopic slide, the slide including a reference area and a specimen cell object area for receipt of specimen cell objects, the reference cell area containing a reference means for staining, the reference means having predetermined physical characteristics which are detectable after staining; and
one or more containers of stain material; the stain material including stain for simultaneous stain application to the specimen cell objects and the reference means, the stain in the containers being in an effective amount to provide an optical density to the reference means after staining for a predetermined time such that the optical density of the reference means will be substantially a linear function of stain concentration of the reference means after staining to determine a relationship between the stained reference means and the specimen cell objects to calibrate the instrument being used to study the specimen cell.

2. A kit as recited in claim 1 wherein the kit further contains a rinse sulfonating agent.

3. A kit as recited in claim 1 wherein the reference means includes a monoclonal antibody associated therewith.

4. A kit as recited in claim 2 wherein the stain material includes Azure A in an effective amount to provide an aqueous solution with a concentration of Azure A in a range from about 4.9 to about 5.1 mg/ml when mixed with a 0.1N HCl aqueous solution.

5. A kit as recited in claim 4 wherein the stain material further includes a stain sulfonating agent.

6. A kit as recited in claim 3 wherein the stain includes an enzyme stain.

7. A kit as recited in claim 5 wherein the rinse sulfonating agent is $K_2S_2O_5$ or $Na_2S_2O_5$.

8. A kit as recited in claim 7 wherein the stain sulfonating agent is $K_2S_2O_5$ or $Na_2S_2O_5$.

9. A kit as recited in claim 1 wherein the stain is selected from the group consisting of Azure A, congo red, pararosanilin, hematoxylin, eosin, methyl green, diaminobenzidine, alkaline phosphatase, methylene blue, giemsa and mixtures thereof.

10. A kit as recited in claim 1 wherein the microscopic slide further includes an optical density reference area, the optical density reference area including a material having a predetermined known optical density to calibrate the slide with an instrument being used to study the specimen cells.

11. A kit as recited in claim 4 wherein the microscopic slide further includes an optical density reference area, the optical density reference area including a material having a predetermined known optical density to calibrate the slide with an instrument being used to study the specimen cells.

12. A kit for the quantitation of nuclear DNA by light microscopy, the kit comprising:
a microscopic slide, the slide including a reference area and a specimen cell object area for receipt of specimen cell objects, the reference area containing a reference means for staining, the reference means having physical characteristics which permit the reference means to associate with a stain proportionally to an association of the stain with DNA;
one or more containers of stain material, the stain material including a stain for simultaneous stain application to the specimen cell objects and the reference means, the stain in the containers selected from the group consisting of Azure A, pararosanilin, and mixtures thereof in an effective amount to provide an optical density to the reference means after staining for a predetermined time such that the optical density of the reference means will be substantially a linear function of stain concentration of the reference means after staining to determine a relationship between the stained reference means and the specimen cell objects to calibrate the instrument being used to study the specimen cell.

13. A kit as recited in claim 12 further comprising a rinse sulfonating agent.

14. A kit as recited in claim 13 wherein the stain material includes Azure A in an effective amount to provide an aqueous solution with concentration of Azure A in a range of from about 4.9 to about 5.1 mg/ml when the Azure A is mixed with a 0.1N HCl aqueous solution.

15. A kit as recited in claim 14 wherein the stain material further includes a stain sulfonating agent.

16. A kit as recited in claim 14 wherein the rinse sulfonating agent is $K_2S_2O_5$ or $Na_2S_2O_5$.

17. A kit as recited in claim 12 wherein the microscopic slide further includes an optical density reference area, the optical density reference area including a material having a predetermined known optical density to calibrate the slide with an instrument being used to study the specimen cells.

18. A kit as recited in claim 14 wherein the microscopic slide further includes an optical density reference area, the optical density reference area including a material having a predetermined known optical density to calibrate the slide with an instrument being used to study the specimen cells.

19. A kit as recited in claim 12 wherein the reference means includes a reference material which is selected from the group consisting of trout erythrocytes, chicken erythrocytes, dried DNA, cultured cell lines and mixtures thereof.

20. A kit as recited in claim 14 wherein the reference means includes a reference material which is selected from the group consisting of trout erythrocytes, chicken erythrocytes, dried DNA, cultured cell lines and mixtures thereof.

21. A kit as recited in claim 15 wherein the reference means includes a reference material which is selected from the group consisting of trout erythrocytes, chicken erythrocytes, dried DNA, cultured cell lines and mixtures thereof.

22. A kit as recited in claim 1 wherein the reference means includes a reference material which is selected from the group consisting of trout erythrocytes, chicken erythrocytes, dried DNA, cultured cell lines and mixtures thereof.

23. A kit as recited in claim 4 wherein the reference means includes a reference material which is selected from the group consisting of trout erythrocytes, chicken erythrocytes, dried DNA, cultured cell lines and mixtures thereof.

24. A kit as recited in claim 9 wherein the reference means includes a reference material which is selected from the group consisting of trout erythrocytes, chicken erythrocytes, dried DNA, cultured cell lines and mixtures thereof.

25. A kit as recited in claim 1 wherein the stain is selected from the group consisting essentially of thionin, Azure A, Azure C, pararosanilin, acriflavine, diaminobenzidine, alkaline phosphatase, eosin, methyl green, ethyl green, fast green, methylene blue, hematoxylin, acridine orange, giemsa and mixtures thereof.

26. A kit for the quantitation of nuclear DNA by light microscopy, the kit comprising:
a microscopic slide, the slide including a reference area and a specimen cell object area for receipt of specimen cell objects, the reference area containing a reference means for staining, the reference means having physical characteristics which permit the reference means to associate with a stain proportionally to an association of the stain with DNA;
one or more containers of stain material, the stain material including a stain for simultaneous stain application to the specimen cell objects and the reference means, the stain in the containers selected from the group consisting of thionin, Azure A, Azure C, pararosanilin, acriflavine and mixtures thereof in an effective amount to provide an optical density to the reference means after staining for a predetermined time such that the optical density of the reference means will be substantially a linear function of stain concentration of the reference means after staining to determine a relationship between the stained reference means and the specimen cell objects to calibrate the instrument being used to study the specimen cell.

27. A kit as recited in claim 25 wherein the reference means includes a reference material which is selected from the group consisting of rat liver nuclei, trout erythrocytes, chicken erythrocytes, dried DNA, cultured cell lines and mixtures thereof.

28. A kit as recited in claim 26 wherein the reference means includes a reference material which is selected from the group consisting of rat liver nuclei, trout erythrocytes, chicken erythrocytes, dried DNA, cultured cell lines and mixtures thereof.

29. A kit for the quantitation of cell nuclei as recited in claim 1 wherein the stain is thionin and the kit is for the quantitation of nuclear DNA by light microscopy.

30. A kit as recited in claim 29 wherein the optical density of the reference means after staining is in the range of from about 0.1 to about 0.8.

31. A kit as recited in claim 30 wherein the reference means includes a reference material which is selected from the group consisting of rat liver nuclei, trout erythrocytes, chicken erythrocytes, dried DNA, cultured cell lines and mixtures thereof.

32. A kit for the quantitation of cell nuclei as recited in claim 1 wherein the kit is for the quantitation of nuclear DNA by light microscopy and the reference means includes rat liver nuclei.

33. A kit for the quantitation of cell nuclei as recited in claim 32 wherein the stain material includes thionin in an effective amount to provide an aqueous solution with a concentration of thionin in a range of from about 1 to about 5 mg/ml when mixed with 0.1N HCl.

34. A kit as recited in claim 32 wherein the microscopic slide further includes an optical density reference area, the optical density reference area including a material having a predetermined known optical density to calibrate the slide with an instrument being used to study the specimen cells.

35. A kit as recited in claim 33 wherein the optical density of the reference means after staining is in the range of from about 0.1 to about 0.8.

36. A kit as recited in claim 12 wherein the optical density of the reference means after staining is in the range of from about 0.1 to about 0.8.

37. A kit as recited in claim 26 wherein the optical density of the reference means after staining is in the range of from about 0.1 to about 0.8.

* * * * *

UNITED STATES PATENT AND TRADEMARK OFFICE
CERTIFICATE OF CORRECTION

PATENT NO. : 5,109,429
DATED : April 28, 1992
INVENTOR(S) : Bacus, et. al.

It is certified that error appears in the above-indentified patent and that said Letters Patent is hereby corrected as shown below:

On the Title page, item [56] under U. S. Patent Documents "Weber et al.", change "3,977,971" to -- 3,977,791--.
On the Title page, item [56] under U. S. Patent Documents col. 2, line 16, "Dolbeare" should be numbered --4,345,027-- and dated --8/82--.

Column 1, line 65, change "skill" to --state--.

Column 3, line 41, change "Corrrelated" to --Correlated--.

Column 5, line 29, change "a" to --as--.

Column 11, line 26, change "are" to --or--.

Column 13, line 39, after "for" insert --deviation of the stain from a perfect staining for which--.

Column 14, line 38, change "the" to --an--.

Column 15, line 28, change "the" to --an--.

UNITED STATES PATENT AND TRADEMARK OFFICE
CERTIFICATE OF CORRECTION

PATENT NO. : 5,109,429
DATED : April 28, 1992
INVENTOR(S) : Bacus, et. al.

It is certified that error appears in the above-indentified patent and that said Letters Patent is hereby corrected as shown below:

Column 16, line 44, change "the" to --an--.

Signed and Sealed this

Eleventh Day of January, 1994

*Attest:*

BRUCE LEHMAN

*Attesting Officer*  *Commissioner of Patents and Trademarks*